(12) United States Patent
Tokarski et al.

(10) Patent No.: US 7,166,400 B2
(45) Date of Patent: Jan. 23, 2007

(54) ORGANOPHOTORECEPTOR WITH A HYDRAZONE POLYMER CHARGE TRANSPORT MATERIAL

(75) Inventors: Zbigniew Tokarski, Woodbury, MN (US); Nusrallah Jubran, St. Paul, MN (US); Kam W. Law, Woodbury, MN (US)

(73) Assignee: Samsung Electronics Co., Ltd., Suwon (KR)

( * ) Notice: Subject to any disclaimer, the term of this patent is extended or adjusted under 35 U.S.C. 154(b) by 153 days.

(21) Appl. No.: 10/695,044

(22) Filed: Oct. 28, 2003

(65) Prior Publication Data

US 2005/0089783 A1    Apr. 28, 2005

(51) Int. Cl.
*G03G 5/05* (2006.01)

(52) U.S. Cl. .................. 430/73; 430/58.35; 430/79; 430/96; 399/159

(58) Field of Classification Search ............. 430/58.35, 430/73, 79, 96; 399/159
See application file for complete search history.

(56) References Cited

U.S. PATENT DOCUMENTS

| | | | |
|---|---|---|---|
| 4,214,907 A | 7/1980 | Nakazawa et al. | |
| 4,388,392 A | 6/1983 | Kato et al. | |
| 4,444,860 A | 4/1984 | Yasujima et al. | |
| 4,490,452 A | 12/1984 | Champ et al. | |
| 4,574,114 A | 3/1986 | Tsutsumi et al. | |
| 4,937,165 A | 6/1990 | Ong et al. | |
| 5,011,906 A | 4/1991 | Ong et al. | |
| 5,232,801 A | 8/1993 | Rule et al. | |
| 5,232,802 A | 8/1993 | Rule et al. | |
| 5,248,578 A | 9/1993 | Takaoka et al. | |
| 6,864,025 B1 * | 3/2005 | Law et al. ................. | 430/58.6 |

FOREIGN PATENT DOCUMENTS

| | | |
|---|---|---|
| DE | 816923 | 7/1959 |
| EP | 1420303 | 5/2004 |
| EP | 1465020 | 10/2004 |
| JP | 2001-166519 | 6/2001 |

OTHER PUBLICATIONS

"Synthesis, Characterization and Binding Properties of Epoxy Resins Based on Carbonohydrazones and Thiocarbonohydrazones", by P.M. Thangamathesvaran and S.R. Jain, Frontiers of Polymer Research, p. 589-594, Edited by P.N. Prasad and J.K. Nigam, Plenum Press, NY, 1991.

"Novel Energetic N-N Bonded Polymeric Binders for Composite Propellants," by S.R.Jain et al, Macromolecules New Frontiers, p. 1018-1021, Allied Publishers Ltd., New Delhi, 1998.

\* cited by examiner

*Primary Examiner*—John L Goodrow
(74) *Attorney, Agent, or Firm*—Patterson, Thuente, Skaar & Christensen, P.A.

(57) ABSTRACT

An organophotoreceptor comprises an electrically conductive substrate and photoconductive element on the electrically conductive substrate, the photoconductive element having a) a charge transport material with the formula

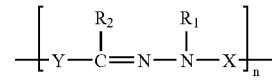

where X is a linking group having the formula $-(CH_2)_m-$, branched or linear, where m is an integer between 0 and 20, inclusive, and one or more of the methylene groups is optionally replaced by O, S, C=O, O=S=O, a heterocyclic group, an aromatic group, urethane, urea, an ester group, a $NR_3$ group, a $CHR_4$ group, or a $CR_5R_6$ group where $R_3$, $R_4$, $R_5$, and $R_6$ are, independently, H, hydroxyl group, thiol group, an alkyl group, an alkaryl group, a heterocyclic group, or an aryl group;

$R_1$ and $R_2$ are independently a hydrogen, a halogen, an alkyl group, an aryl group, an alkaryl group, an aromatic group or a heterocyclic group;

Y is an aromatic group; and n is a distribution of integer values greater than 2; and (b) a charge generating compound.

The charge transport material can be crosslinked with a polymer binder either directly or through a crosslinking agent.

19 Claims, No Drawings

ORGANOPHOTORECEPTOR WITH A HYDRAZONE POLYMER CHARGE TRANSPORT MATERIAL

FIELD OF THE INVENTION

This invention relates to organophotoreceptors suitable for use in electrophotography and, more specifically, to organophotoreceptors having a charge transport material comprising a polymer having a hydrazone group and an aromatic group in the repeating unit. Furthermore, the invention further relates to methods for forming an organophotoreceptor with a polymer comprising a hydrazone group and an aromatic group.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising a) a charge transport material having the formula:

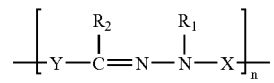

where X is a linking group having the formula $—(CH_2)_m—$, branched or linear, where m is an integer between 0 and 20, inclusive, and one or more of the methylene groups is optionally replaced by O, S, C=O, O=S=O, a heterocyclic group, an aromatic group, urethane, urea, an ester group, a $NR_3$ group, a $CHR_4$ group, or a $CR_5R_6$ group where $R_3$, $R_4$, $R_5$, and $R_6$ are, independently, H, hydroxyl group, thiol group, an alkyl group, an alkaryl group, a heterocyclic group, or an aryl group;

$R_1$ and $R_2$ are independently a hydrogen, a halogen, an alkyl group, an aryl group, an alkaryl group, an aromatic group or a heterocyclic group;

Y is an aromatic group, such as a (N,N-disubstituted) arylamine group; and n is a distribution of integer values greater than 2; and (b) a charge generating compound.

The organophotoreceptor may be provided in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that includes (a) a light imaging component; and (b) the above-described organophotoreceptor oriented to receive light from the light imaging component. The apparatus preferably further includes a toner dispenser, such as liquid toner dispenser. The method of electrophotographic imaging with photoreceptors containing these novel charge transport compounds is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features desirable charge transport materials having the general formula shown above.

In a fifth aspect, the invention features a method for forming a polymeric charge transport material by the polymerization reaction of monomers having the formula:

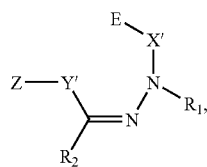

where X' is a linking group having the formula —(CH$_2$)$_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, a NR$_3$ group, a CHR$_4$ group, or a CR$_5$R$_6$ group where R$_3$, R$_4$, R$_5$, and R$_6$ are, independently, H, hydroxyl group, thiol group, an alkyl group, an alkaryl group, a heterocyclic group, or an aryl group;

R$_1$ and R$_2$ are independently a hydrogen, a halogen, an alkyl group, an aryl group, an alkaryl group, an aromatic group or a heterocyclic group;

Y' is an aromatic group;

Z is a first reactive functional group; and

E is a second reactive functional group that can covalently bond with the first reactive functional group Z. In some embodiments, the first reactive functional group is selected from the group consisting of hydroxyl group, carboxyl group, amino group, and thiol group. The second reactive functional group can be an epoxy group. The polymerization reaction can be initiated, for example, by appropriately adjusting the pH or other appropriate change of conditions.

In a further aspect, the invention features a composition having the formula:

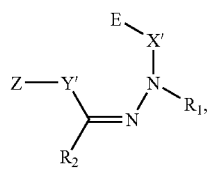

where X' is a linking group having the formula —(CH$_2$)$_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, a NR$_3$ group, a CHR$_4$ group, or a CR$_5$R$_6$ group where R$_3$, R$_4$, R$_5$, and R$_6$ are, independently, H, hydroxyl group, thiol group, an alkyl group, an alkaryl group, a heterocyclic group, or an aryl group;

R$_1$ and R$_2$ are independently a hydrogen, a halogen, an alkyl group, an aryl group, an alkaryl group, an aromatic group or a heterocyclic group;

Y' is an aromatic group;

Z is a first reactive functional group; and

E is a second reactive functional group that can covalently bond with the first reactive functional group Z. This composition is suitable for forming a polymer charge transport material, as described herein.

These photoreceptors can be used successfully with toners, such as liquid toners, to produce high quality images. The high quality of the imaging system is maintained after repeated cycling.

Other features and advantages of the invention will be apparent from the following description of the preferred embodiments thereof, and from the claims.

DETAILED DESCRIPTION OF PREFERRED EMBODIMENTS

Polymers with desirable properties as charge transport materials have repeat units comprising a hydrazone group linked with at least one aromatic group. These charge transport materials can have desirable properties for use within organophotoreceptors for electrophotography. In particular, the charge transport compounds of this invention can have high charge carrier mobilities and good compatibility with various binder materials, can be incorporated in both the single and multilayer photoconductive elements, and can possess excellent electrophotographic properties. The organophotoreceptors according to this invention generally can have a high photosensitivity, a low residual potential, and a high stability with respect to cycle testing, crystallization, and organophotoreceptor bending and stretching. The organophotoreceptors are particularly useful in laser printers and the like as well as photocopiers, scanners and other electronic devices based on electrophotography. The use of these charge transport compounds is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as charge transport compound or electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, triaryl amines, polyvinyl carbazole, polyvinyl pyrene, polyacenaphthylene, or multi-hydrazone compounds comprising at least two hydrazone groups and at least two groups selected from the group consisting of p-(N,N-disubstituted) arylamine such as triphenylamine and heterocycles such as carbazole, julolidine, phenothiazine, phenazine, phenoxazine, phenoxathiin, thiazole, oxazole, isoxazole, dibenzo(1,4)dioxine, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Generally, an electron transport composition has an electron affinity that is large relative to potential electron traps while yielding an appropriate electron mobility in a composite with a polymer. In some embodiments, the electron transport composition has a reduction potential less than $O_2$. In general, electron transport compositions are easy to reduce and difficult to oxidize while charge transport compositions generally are easy to oxidize and difficult to reduce. In some embodiments, the electron transport compounds have a room temperature, zero field electron mobility of at least about $1 \times 10^{-13}$ cm$^2$/Vs, in further embodiments at least about $1 \times 10^{-10}$ cm$^2$/Vs, in additional embodiments at least about $1 \times 10^{-8}$ cm$^2$/Vs, and in other embodiments at least about $1 \times 10^{-6}$ cm$^2$/Vs. A person of ordinary skill in the art will recognize that other ranges of electron mobility within the explicit ranges are contemplated and are within the present disclosure.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene)thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl)methylene]anthrone, 1,8-dihydroxy-110-[bis(ethoxycarbonyl)methylene]anthrone, and 1-cyano-10-[bis(ethoxycarbonyl)methylene]anthrone, 7-nitro-2-aza-9-fluroenylidenemalononitrile, diphenoquinone derivatives, benzoquinone derivatives, naphtoquinone derivatives, quinine derivatives, tetracyanoethylenecyanoethylene, 2,4,8-trinitrothioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromomaleic anhydride, pyrene derivatives, carbazole derivatives, hydrazone derivatives, N,N-dialkylaniline derivatives, diphenylamine derivatives, triphenylamine derivatives, triphenylmethane derivatives, tetracyanoquinodimethane, 2,4,5,7-tetranitro-9-fluorenone, 2,4,7-trinitro-9-dicyanomethylenefluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene)malononitrile derivative, such as (4-n-butoxycarbonyl-9-fluorenylidene)malononitrile.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein can be effective at transporting charge, holes and/or electrons, from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

Improved multifunctional compositions can function as monomers for incorporation into polymeric charge transport materials. The polymeric charge transport materials can be formed from polymerization of the monomers and subsequent incorporation into an organophotoreceptor, which can involve combination with a binder and/or other elements of a layer of an organophotoreceptor. In additional or alternative embodiments, polymerization of the monomer units can be performed in the presence of a crosslinkable polymer binder for the formation of a crosslinked polymer involving the charge transport polymer intimately crosslinked with the binder as an integrated composite.

The monomer units have two or more functional groups with at least one of the functional groups being reactive to bind with a second functional group. In some embodiments, one of the functional groups is an epoxy group while a second group contains an active hydrogen for binding with the epoxy group. The monomer compound can be represented with the following formula:

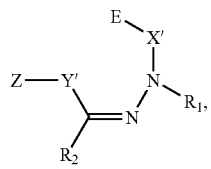

where Z is a first functional group and E is a second functional group that can bond with Z under appropriate conditions. $R_1$, $R_2$, X', Y', Z and E are described further below.

The monomer can be polymerized under appropriate conditions to form a polymeric charge transport material. The polymeric charge transport material can be represented by the following formula:

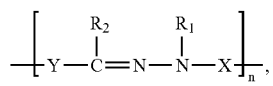

where the integer n represents a distribution of values corresponding to the degree of polymerization as is well understood generally in the chemical arts relating to polymers. The polymer can be a homopolymer or a polymer crosslinked with a binder polymer to provide a polymer composite that can provide a stable layer for an organophotoreceptor element. When forming a crosslinked polymer, a functional group of the charge transport material monomer may directly bond with a function group of the binder or indirectly through a crosslinking agent that crosslinks the charge transport material with the binder. A suitable crosslinking agent has suitable multiple functionality to react with a functional group of the charge transport material and a functional group of the binder. The homopolymer as well as the polymer crosslinked with a polymer binder can be represented by the formula above.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, phenyl group, aromatic group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents such as hydroxyethyl, cyanobutyl, 1,2,3-trichloropropane, and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, ortho-cyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Similarly, when referring to epoxy group, the compound or substituent cited includes any substitution that does not substantively alter the chemical nature of the epoxy ring in the formula. When referring p-(N,N-disubstituted)arylamine group, the two substituents attached to the nitrogen may be any group that will not substantively alter the chemical nature of the amine group. When referring to an aromatic group, the substituent cited can include any substitution that does not substantively alter the chemical nature of the 4n+2 pi electron system in the aromatic group. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material, such as a charge transport compound or an electron transport compound, in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (Stabar™ S-100, available from ICI), polyvinyl fluoride (Tedlar®, available from E.I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodine, conductive polymers such as polypyrroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material which is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the tradename Indofast® Double Scarlet, Indofast® Violet Lake B, Indofast® Brilliant Scarlet and Indofast® Orange, quinacridones available from DuPont under the tradename Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425, 333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

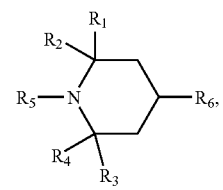

-continued

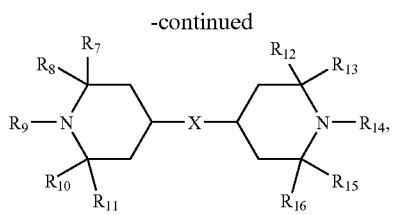

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, independantly, hydrogen, alkyl group, or ester, or ether group; and $R_5$, $R_9$, and $R_{14}$ are, independently, alkyl group; and X is a linking group selected from the group consisting of —O—CO—$(CH_2)_m$—CO—O— where m is between 2 to 20.

The binder generally is capable of dispersing or dissolving the charge transport material (in the case of the charge transport layer or a single layer construction), the charge generating compound (in the case of the charge generating layer or a single layer construction) and/or a second charge transport material for appropriate embodiments. Examples of suitable binders for both a charge generating layer and a charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly (hydroxyether) resins, polyhydroxystyrene resins, novolak, poly(phenylglycidyl ether)-co-dicyclopentadiene, copolymers of monomers used in the above-mentioned polymers, and combinations thereof.

In some embodiments, the binder comprises a polymer with a reactive functional group that bonds with a reactive functional group of the polymeric charge transport material or correspondingly with a reactive functional group of the monomer that polymerizes to form the polymeric charge transport material. For embodiments in which the monomer has an epoxy group, the polymer binder can comprise an active hydrogen functionality, such as hydroxyl, thiol, amino (primary amino or secondary amino), a carboxyl group or a combination thereof, that can react with the epoxy ring of the charge transport material or corresponding monomer. In some embodiments, the polymer binder reacts with a functional group of a crosslinking agent, such as a cyclic acid anhydride. In the organophotoreceptor, the functional group of the polymer can be bonded directly with the epoxy group or indirectly through a co-reactive crosslinking agent, for example, a cyclic acid anhydride group, to form the corresponding and predictable reaction product.

Suitable binders with reactive functionality include, for example, polyvinyl butyral, such as BX-1 and BX-5 form Sekisui Chemical Co. Ltd., Japan.

Optionally, the photoconductive layer may comprise a crosslinking agent linking the charge transport compound and the binder. As is generally true for crosslinking agents in various contexts, the crosslinking agent comprises a plurality of functional groups or at least one functional group with the ability to exhibit multiple functionality. In embodiments with a charge transport material having an epoxy functional group, a suitable crosslinking agent can comprise at least one functional group that reacts with an epoxy group and at least one functional group reactive with a functional group of the polymer binder. Suitable functional groups for reacting with the epoxy group include, for example, a reactive active hydrogen functionality, such as hydroxyl, thiol, amino (primary amino or secondary amino), a carboxyl group or a combination thereof. In some embodiments, the reactive functional group for reacting with the polymer does not react significantly with the epoxy group. In general, a person of ordinary skill in the art can select the appropriate functional group of the crosslinking agent to react with the binder, or similarly, a person of ordinary skill in the art can select appropriate functional groups of the binder to react with the functional group of the crosslinking agent. Suitable functional groups of the crosslinking agent that do not react significantly with the epoxy group, at least under selected conditions, include, for example, epoxy groups, aldehydes and ketones. Suitable reactive binder functional groups for reacting with the aldehydes and ketones include, for example, amines.

In some embodiments, an optional crosslinking agent is a cyclic acid anhydride, which effectively is at least bifunctional. Non-limiting examples of suitable cyclic acid anhydrides include, for example, 1,8-naphthalene dicarboxylic acid anhydride, itaconic anhydride, glutaric anhydride, citraconic anhydride, fumaric anhydride, phthalic anhydride, isophthalic anhydride, terephthalic anhydride, and maleic anhydride.

Suitable optional additives for any one or more of the layers include, for example, antioxidants, coupling agents, dispersing agents, curing agents, surfactants, and combinations thereof.

The photoconductive element overall typically has a thickness from about 10 to about 45 microns. In the dual layer embodiments having a separate charge generating layer and a separate charge transport layer, the charge generation layer generally has a thickness from about 0.5 to about 2 microns, and the charge transport layer has a thickness from about 5 to about 35 microns. In embodiments in which the charge transport material and the charge generating compound are in the same layer, the layer with the charge generating compound and the charge transport material generally has a thickness from about 7 to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional second charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of concentrations for the dual layer embodiments within the explicit ranges above are contemplated and are within the present disclosure.

For the embodiments with a single layer having a charge generating compound and a charge transport material, the photoconductive layer generally comprises a binder, a charge transport material and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport material and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating material and the charge transport compound may comprise a second charge transport material. The optional charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport compound can advantageously further include a UV light stabilizer. In particular, the electron transport layer generally can comprise an electron transport compound, a binder and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any of one or more appropriate layers of the photoconductor generally is in an amount from about 0.5 to about 25 weight percent and in some embodiments in an amount from about 1 to about 10 weight percent, based on the weight of the particular layer. Furthermore, the optional crosslinking agent, such as a cyclic acid anhydride, in the photoconductive layer can be, when present, in an amount from about 0.1 to about 16 weight percent and in further embodiments in an amount from about 1 to about 15 weight percent, based on the weight of the photoconductive layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, a charge transport material as described herein, a second charge transport material, such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection to the underlayers from abrasion and/or a toner carrier liquid. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

The overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound as described above may be used in a release layer. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors For Liquid Electrophotography," incorporated herein by reference.

Sub-layers can comprise, for example, polyvinylbutyral, organosilanes, hydrolyzable silanes, epoxy resins, polyesters, polyamides, polyurethanes, silicones and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Material

The organophotoreceptor described herein comprise a charge transport material having the formula:

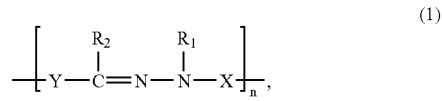

(1)

where X is a linking group having the formula $-(CH_2)_m-$, branched or linear, where m is an integer between 0 and 20, inclusive, and one or more of the methylene groups is optionally replaced by O, S, C=O, O=S=O, a heterocyclic group, an aromatic group, urethane, urea, an ester group, a $NR_3$ group, a $CHR_4$ group, or a $CR_5R_6$ group where $R_3$, $R_4$, $R_5$, and $R_6$ are, independently, H, hydroxyl group, thiol group, an alkyl group, an alkaryl group, a heterocyclic group, or an aryl group;

$R_1$ and $R_2$ are independently a hydrogen, a halogen, an alkyl group, an aryl group, an alkaryl group, an aromatic group or a heterocyclic group;

Y is an aromatic group, such as a (N,N-disubstituted) arylamine group; and n is a distribution of integer values greater than 2.

In general, the distribution of n values depends on the polymerization conditions. The presence of the polymer of formula (1) does not preclude the presence of unreacted monomer and dimers within the organophotoreceptor, although the concentrations of monomers and dimers would generally be small if not extremely small or undetectable. The extent of polymerization, as specified with n, can affect the properties of the resulting polymer. In some embodiments, an average n value can be in the hundreds or thousands, although the average n may be any value of 3 or greater and in some embodiments any value of 5 or greater and in further embodiments the average value of n is 10 or greater. A person of ordinary skill in the art will recognize that additional ranges of average n values are contemplated and are within the present disclosure.

The polymer of formula (1) can be formed from monomers with the formula:

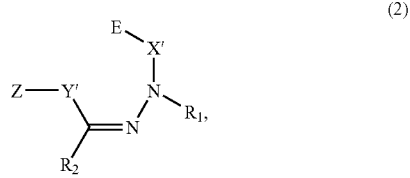

(2)

where X' is a linking group having the formula $—(CH_2)_m—$, branched or linear, where m is an integer between 0 and 20, inclusive, and one or more of the methylene groups is optionally replaced by O, S, C=O, O=S=O, a heterocyclic group, an aromatic group, urethane, urea, an ester group, a $NR_3$ group, a $CHR_4$ group, or a $CR_5R_6$ group where $R_3$, $R_4$, $R_5$, and $R_6$ are, independently, H, hydroxyl group, thiol group, an alkyl group, an alkaryl group, a heterocyclic group, or an aryl group;

$R_1$ and $R_2$ are independently a hydrogen, a halogen, an alkyl group, an aryl group, an alkaryl group, an aromatic group or a heterocyclic group;

Y' is an aromatic group with a first reactive functional group, Z, and E is a second reactive functional group that can covalently bond with the first reactive functional group Z.

In principle, Compound (2) represented by formula (2) can be used as a charge transport material, but the polymerized form, represented by Formula (1), generally would be expected to be more stable. In forming the polymer, the Z and E reactive functional groups react to form a bonded functional group. The bonded functional group can be parsed out in a reasonable way using chemical convention into Z' and E' such that Z'-Y'=Y and X'-E'=X, where X and Y correspond with formula (1). While the parsing of the bonded functional group into Z' and E' may not be unique, there generally are at most a few chemically reasonable ways to parse out the components, and the polymers of formula (1) are equivalent even though specified with slightly different notation.

As a particular example of a reactive functional group, an epoxy group has the following structure

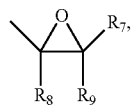

where the unlabeled bond corresponds to the bond to the supporting compound, $R_7$, $R_8$ and $R_9$ are, independently, hydrogen, alkyl group, aryl group or alkaryl group, although $R_8$ and $R_9$ can be fused together to form a 5-member, 6-member, or higher-member ring. The reaction of an epoxy functionality results in a particular chemical structure with a hydroxyl group at a position spaced by one carbon atom relative to a carbon atom bonded to an atom of the binder or crosslinking agent functional group that is involved in a nucleophylic addition at the epoxy functional group. Specifically, the resulting compound has a bonded functional group structure of $U—CR_7R_9CR_8OH—V$, where U comprises a non-carbon atom that gives up a bond to an active hydrogen in the formation of a bond with the epoxy. For convenience, the bonded epoxy functionality $U—CR_7R_9CR_8OH—V$ is referred to herein as an epoxy linkage, which is further a chemical group as used herein. If this reaction forms a unit of the polymer of formula (1), $CR_7R_9CR_8OH—V$ can be associated generally with either Y or X, and U is associated with the other member of Y or X, as appropriate, although other parses of the structure may be possible. In other embodiments, U may be the reacted portion of a functional group associated with the polymer binder or crosslinking agent.

As noted above, the polymeric charge transport material of formula (1) may be crosslinked with a polymer binder directly or through a crosslinking agent. Such crosslinking to the binder can stabilize the organophotoreceptor structure and distribution of charge transport material within the structure. The detailed nature of the structure generally depends on the approach for performing the crosslinking. Nevertheless, the resulting crosslinked structure comprises units with the structure of formula (1) embedded within the crosslinked composite. The degree of crosslinking generally affects the physical properties of the crosslinked composite. The degree of crosslinking generally can be controlled by the nature of the polymer binder and the processing conditions used to perform the crosslinking.

Optionally, the photoconductive layer may comprise a crosslinking agent linking the charge transport compound and the binder. As is generally true for crosslinking agents in various contexts, the crosslinking agent comprises a plurality of functional groups or at least one functional group with the ability to exhibit multiple functionality. Specifically, a suitable crosslinking agent generally comprises at least one functional group that reacts with at least one functional group of the monomer of formula (2) and at least one functional group reactive with a functional group of the polymer binder. For appropriate embodiments, suitable functional groups for reacting, for example, with an epoxy group include, for example, a reactive active hydrogen functionality, such as hydroxyl, thiol, amino (primary amino or secondary amino), a carboxyl group or a combination thereof. In some embodiments, the reactive functional group for reacting with the polymer does not react significantly with the epoxy group. Suitable functional groups of the crosslinking agent that do not react significantly with the epoxy group, at least under selected conditions, include, for example, epoxy groups, aldehydes and ketones. Suitable reactive binder functional groups for reacting with the aldehydes and ketones include, for example, amines. In general, a person of ordinary skill in the art can select the appropriate functional group of the crosslinking agent to react with the binder, or similarly, a person of ordinary skill in the art can select appropriate functional groups of the binder to react with the functional group of the crosslinking agent.

With respect to the Y aromatic group, various aromatic groups have been found to be particularly useful in the formation of charge transport materials. Examples of these useful aromatic groups include N,N-disubstituted arylamine groups, such as, carbazole groups, julolidine groups, and p-(N,N-disubstituted) aryl amine groups (e.g., triphenyl amine), aromatic heterocyclic groups, such as pyrrolyl groups, tetrazolyl groups, and benzotriazolyl groups, and aryl groups, such as phenyl groups, naphthyl groups, and stilbenyl groups.

Synthesis of Charge Transport Materials

Synthesis of the charge transport material generally involves two steps, the formation of the monomer and the polymerization of the monomer. The monomer and the corresponding polymer repeat unit has a hydrazone bonded to an aromatic group. The synthesis of the monomer can be complicated by the presence of at least two reactive functional groups. However, existing approaches of organic synthesis involving the temporary presence of protecting groups to prevent the undesired reaction of a functional group during the synthesis of the remaining portion of the compound. The polymerization reaction can be based on conventional polymer chemistry.

The synthesis of the hydrazone generally can be based on the reaction of a substituted hydrazine with an aromatic aldehyde or ketone. The aromatic aldehyde/ketone can be derivatized to form at least one functional group of the monomer, which is the Z group of formula (2), while other portions of the aromatic aldehyde form Y'. The hydrazone or hydrazine, if performed prior to the formation of the hydrazone, can be derivatized at the appropriate nitrogen to form the X'-E group of formula (2). One or both of the functional groups can be protected during appropriate portions of the synthesis to prevent undesirable reaction of the functional group.

Specifically, a hydrazine can be reacted with an appropriate aromatic aldehyde or ketone to form a desired hydrazone charge transfer compound. The reactions can be catalyzed, for example, with an appropriate amount of concentrated acid, in particular sulfuric acid. After mixing in the catalytic amount of acid with the hydrazine and aromatic aldehyde, the mixture can be refluxed for about 2 hours to about 16 hours. The initial product can be purified by recrystallization.

In some embodiments, a derivatized hydrazine may be obtained in an acidified hydrochloride form. For these embodiments, the hydrazine hydrochloride can be reacted with an aqueous carbonate base while stirring the mixture, prior to formation of the hydrazone. An excess of carbonate base can be added, such as 1.2 moles of potassium carbonate for embodiments with one mole of hydrazine hydrochloride per mole hydrazine or 2.4 moles of potassium carbonate for embodiments with one mole of hydrazine dihydrochloride per mole hydrazine.

In some embodiments of interest, the E group is an epoxy group. For example, the aromatic-substituted secondary amine of the hydrazone reacts with the epichlorohydrin by way of the active hydrogen of the secondary amine in a base catalyzed reaction to form the epoxy group with a —$CH_2$— group (as the X'-group of formula (2)) between the epoxy group and the amine. Alternatively, other X' groups can be formed, for example, using bifunctional group with a halogen and with a vinyl group (C=C) or substituted vinyl group. The halide group can be replaced by a bond to the secondary amine group of the hydrazone by a nucleophilic substitution. The vinyl or substituted vinyl group can be converted to the epoxy group in a epoxidation reaction, for example, by the reaction with perbenzoic acid or other peroxy acid, in an electrophilic addition reaction. Thus, the identity of X can be selected as desired through the introduction of a difunctional compound with a halide group and a vinyl/substituted-vinyl group.

If E is an epoxy group, suitable Z groups of formula (2) include, for example, hydroxyl, thiol, amino (primary amino or secondary amino), a carboxyl group or a combination thereof. The Z group can be protected during the formation of the epoxy group.

As noted above, an epoxy group can be reacted with the Z group of the monomer to form the polymer charge transport material or with functional groups of a polymer binder directly or through a crosslinking agent. The reactions of epoxy groups with appropriate functional groups are described further in C. A. May, editor, "Epoxy Resins Chemistry And Technology," (Marcel Dekker, New York, 1988) and in B. Ellis, editor, "Chemistry And Technology Of Epoxy Resins," (Blackie Academic And Professional, London, 1993), both of which are incorporated herein by reference.

Hydrazines

While a range of hydrazone compounds are consistent with formulas (1) and (2), the properties of many charge transport materials have benefited from the presence of additional aromatic groups within the compounds. Thus, in some embodiments, it may be desired to have $R_1$ and/or $R_2$ of formulas (1) and (2) to be aromatic groups. For the formation of compounds with an aromatic $R_1$ group, the syntheses of some representative hydrazines are described as follows.

1,1-Dinaphthylhydrazine 1,1-Dinaphthylhydrazine can be prepared according to the procedure described in Staschkow, L. I.; Matevosyan, R. O. Journal of the General Chemistry (1964) 34, 136, which is incorporated herein by reference. A suspension of 0.07 mole of the naphthyl nitrosamine in 750 ml of ether is cooled to 5–8° C. and treated with 150 g of zinc dust. Acetic acid (70 ml) is then added drop-wise with stirring. To complete the reaction, 40 g of zinc dust is added. The reaction mixture is heated and filtered from the sludge. The mother liquor is washed with 10% sodium carbonate solution and dried with solid potassium hydroxide (KOH). The ether is distilled off to give the crystalline hydrazine, which is crystallized from ethanol or butanol. Other symmetric disubstituted hydrazines can be synthesized based on an equivalent process.

N-Phenyl-N-sulfolan-3-ylhydrazine

N-Phenyl-N-sulfolan-3-ylhydrazine can be prepared according to the procedure described in Great Britain Patent No. 1,047,525 by Mason, which is incorporated herein by reference. To a mixture of 0.5 mole of butadiene sulfone (commercially available from Aldrich, Milwaukee, Wis.) and 0.55 mole of phenylhydrazine (commercially available from Aldrich, Milwaukee, Wis.) was added 0.005 mole 40% aqueous potassium hydroxide solution. The mixture was kept for 2 hours at 60° C. whereupon a solid separated. After 10 hours the solid was filtered off to give N-phenyl-N-sulfolan-3-ylhydrazine (53%) having a melting point of 120–121° C. (recrystallized from methanol).

N-Pyrrol-2-yl-N-phenylhydrazine

N-Pyrrol-2-yl-N-phenylhydrazine can be prepared according to the procedure described in Japanese Patent No. 05148210 by Myamoto, incorporated herein by reference.

1-Phenyl-1-(1-benzyl-1H-tetrazol-5-yl)hydrazine

1-Phenyl-1-(1-benzyl-1H-tetrazol-5-yl)hydrazine can be prepared according to the procedure described in Tetrahedron (1983), 39(15), 2599–2608 by Atherton et al., incorporated herein by reference.

N-(4-Stilbenyl)-N-phenylhydrazine

N-(4-Stilbenyl)-N-phenylhydrazine can be prepared according to the procedure described in Zh. Org. Khim. (1967), 3(9), 1605–1613 by Matevosyan et al., incorporated herein by reference. Following this procedure, to a mixture of phenylhydrazine (97 g, 0.9 mole, commercially available from Aldrich, Milwaukee, Wis.) and p-chlorostilbene (21.4 g, 0.1 mole, commercially available from Spectrum Quality Products, Inc., Gardena, Calif.; Web: www.spectrumchemical.com) heated to boiling temperature, sodium was slowly added until there was no more discharge of red coloration. After boiling for some time the mixture was dissolved in 1750 ml of ethanol and cooled to −15° C. The precipitated product was recrystallized to give 28% of N-(4-stilbenyl)-N-phenylhydrazine.

N-(5-Benzotriazolyl)-N-phenylhydrazine

N-(5-benzotriazolyl)-N-phenylhydrazine can be prepared according to the procedure that follows. To a mixture of phenylhydrazine (97 g, 0.9 mole, commercially available from Aldrich, Milwaukee, Wis.) and 5-chlorobenzotriazole (15.4 g, 0.1 mole, commercially available from Aldrich, Milwaukee, Wis.) heated to boiling temperature, sodium is slowly added until there is no more discharge of red coloration. After boiling for some time the mixture is cooled to room temperature. The product is isolated and purified.

N-Phenyl-N-sulfolan-3-ylhydrazine

N-Phenyl-N-sulfolan-3-ylhydrazine can be prepared according to the procedure described in Great Britain Patent No. 1,047,525 by Mason, incorporated herein by reference. Following this procedure, to a mixture of 0.5 mole of butadiene sulfone (commercially available from Aldrich, Milwaukee, Wis.) and 0.55 mole of phenylhydrazine (commercially available from Aldrich, Milwaukee, Wis.), a 0.005 mole 40% aqueous potassium hydroxide solution was added. The mixture was kept for 2 hours at 60° C. whereupon a solid separated. After 10 hours the solid was filtered off to give N-phenyl-N-sulfolan-3-ylhydrazine (I) (93%) having a melting point of 119–120° C. (recrystallized from methanol).

N-4-[(9H-fluoren-9-ylidene)benzyl]-N-phenylhydrazine

N-4-[(9H-fluoren-9-ylidene)benzyl]-N-phenylhydrazine can be prepared according to the procedure similar to that described in Zh. Org. Khim. (1967), 3(9), 1605–1613 by Matevosyan et al., incorporated herein by reference. Following this procedure, to a mixture of phenylhydrazine (97 g, 0.9 mole, commercially available from Aldrich, Milwaukee, Wis.) and p-9-(4-chlorobenzylidene)fluorene (28.9 g, 0.1 mole, commercially available from Aldrich, Milwaukee, Wis.) heated to boiling temperature, sodium was slowly added until there was no more discharge of red coloration. After boiling for some time the mixture was dissolved in 1750 ml of ethanol and cooled to −15° C. The precipitated product was recrystallized to give N-4-[(9H-fluoren-9-ylidene)benzyl]-N-phenylhydrazine.

5-Methyl-1-Phenyl-3-(1-Phenylhydrazino)-Pyrazole

5-Methyl-1-phenyl-3-(1-phenylhydrazino)-pyrazole can be prepared according to the procedure described in J. Chem. Soc. C (1971), (12), 2314–2317 by Boyd et al., incorporated herein by reference.

4-Methylsulfonylphenylhydrazine (Registry Number 877-66-7)

4-Methylsulfonylphenylhydrazine is commercially available from Fisher Scientific USA, Pittsburgh, Pa. (1-800-766-7000).

1,1'-(Sulfonyldi-4,1-phenylene)bishydrazine (Registry Number 14052-65-4)

1,1'-(Sulfonyldi-4,1-phenylene)bishydrazine dihydrochloride is commercially available from Vitas-M, Moscow, Russia; (Phone: +7 (095) 939-5737)

Arylaldehydes/Ketone

Representative arylaldehydes for reacting with a hydrazine or hydrazine derivative to form hydrazones can be obtained as follows, and similar ketones can also be used. These arylaldehydes can be derivatized to form the Z functional group bonded to the aromatic Y' of formula (2). One prophetic example of this is described in detail.

Synthesis of Julolidine Aldehyde

Julolidine (100 g, 0.6 moles, commercially obtained from Aldrich Chemicals Co, Milwaukee, Wis. 53201) was dissolved in dimethylformamide (DMF) (200 ml, commercially obtained from Aldrich) in a 500 ml three neck round bottom flask. The flask was cooled to 0° C. in ice bath. $POCl_3$ (107 g, 0.7 mole, Aldrich) was added drop wise while keeping the temperature below 5° C. After the addition of $POCl_3$ was completed, the flask was warmed to room temperature and placed in a steam bath while stirring for a period of 1 hour. The flask was cooled to room temperature and the solution was added slowly to a large excess of distilled water with good agitation. Stirring was continued for additional 2 hours. The solid was filtered off and washed repeatedly with water until the effluent water became neutral. The product was dried in vacuum oven at 50° C. for 4 hours.

Other Aryl Aldehydes

Suitable commercially available (N,N-disubstituted)arylamine aldehydes are available form Aldrich (Milwaukee, Wis.) including, for example, diphenylamino-benzaldehyde (($C_6H_5$)$_2NC_6H_4CHO$) and 9-ethyl-3-carbazolecarboxyaldehyde.

Synthesis of a Carbazole-Hydrazone Derivatized Monomer

The following prophetic example describes the synthesis of an epoxy, hydroxy derivatized carbazole-hydrazone compound. Other desired monomers can be synthesized based on the teachings herein, both this prophetic example and the description above. The synthesis is described with five steps described in the following five reactions.

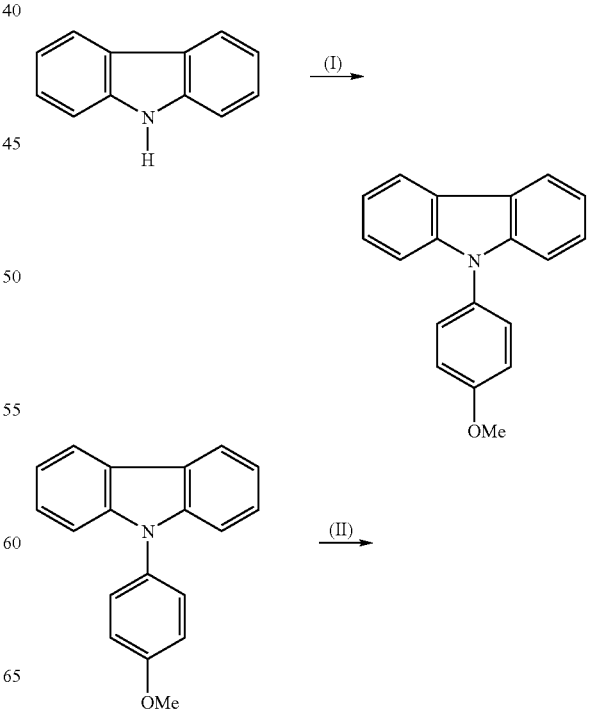

-continued

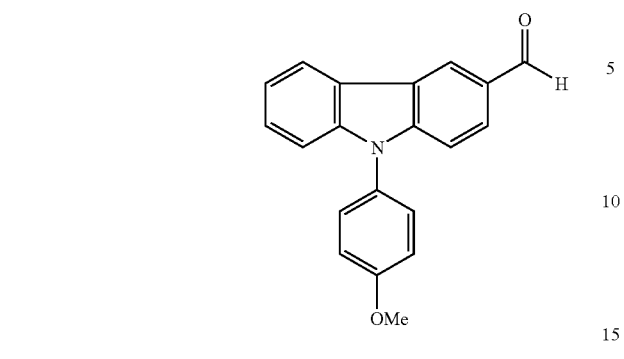

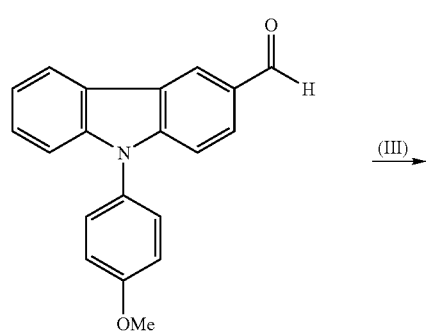

(III) →

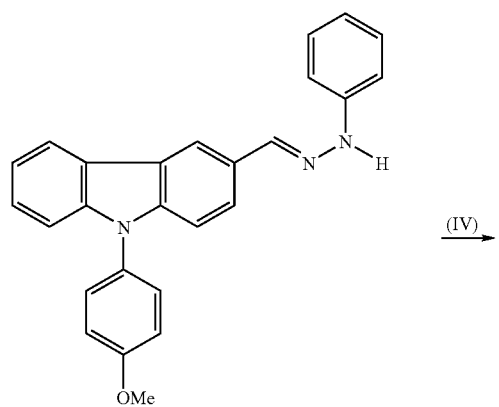

(IV) →

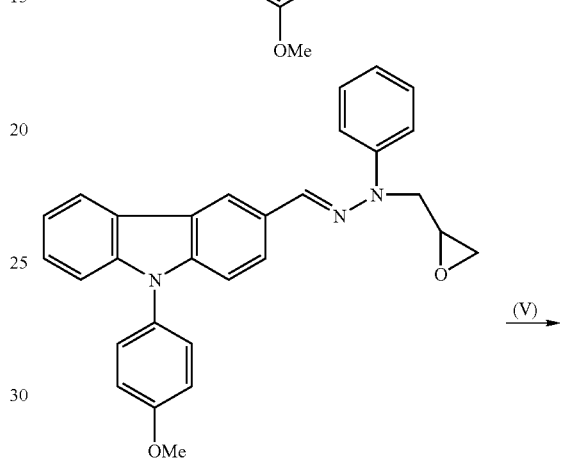

(V) →

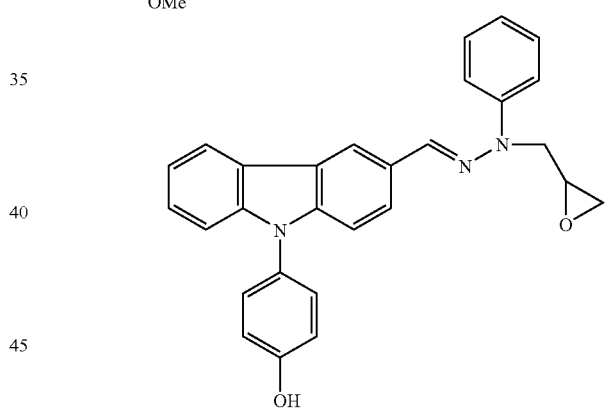

In step (I), carbazole (8.10 g, 48.5 mmole, Aldrich), 4-iodoanisole (12.4 g, 53.5 mmole, Aldrich), copper powder (0.38 g, 6.08 mmole, Aldrich), 18-crown-6-ether (4.28 g, 16.2 mmole, Aldrich), potassium carbonate (7.24 g, 53.4 mmole), 100 ml of o-dichlorobenzene can be added to a 500 ml three neck round bottom flask, equipped with a reflux condenser and a mechanical stirrer. The flask can be placed under dry nitrogen atmosphere and immersed in a silicone oil bath. The flask is then heated at 180° C. for 24 hours. After the reaction is completed, the solution is filtered hot to remove insoluble solids. The filtrate can be concentrated in an evaporator to obtain an oily product, which is added to 200 ml ethanol with stirring. The product can be obtained as a precipitate, which can be collected and recrystallized to obtain the product, which would be expected to be a white solid.

In step (II), dimethylformamide (DMF) is cooled in ice bath at 0° C. Phosphorous oxychloride is added slowly to the DMF while keeping the temperature below 5° C. The intermediate from step (I) is added, and the mixture is heated in a steam bath for 1 hour. The product solid can be isolated and purified.

In step (III), the intermediate from step (II) is dissolved in ethyl alcohol. A slight stochiometric excess of phenylhydrazine is added, and the mixture can be refluxed until thin layer chromatography (TLC) shows the disappearance of the starting material. A product solid can be isolated and recrystallized.

In step (IV), the intermediate from step (III) and epichlorohydrin are added to a 250 ml 3-neck round bottom flask equipped with a reflux condenser, a thermometer and a mechanical stirrer. The reaction mixture can be stirred vigorously at 35–40° C. for 24 h. Six periodically delivered portions of powdered 85% potassium hydroxide and anhydrous sodium sulphate can be added during the reaction time, and the reaction mixture is temporarily cooled to 20–25° C. prior to each addition. After termination of the reaction, the mixture is cooled to room temperature and filtered. The organic phase can be treated with ethyl acetate and washed with distilled water until the wash water is neutral. The organic layer is dried over anhydrous magnesium sulfate, treated with activated charcoal, and filtered. The solvent can then be removed. The residue can be subjected to column chromatography to purify the desired product.

In step (V), the intermediate from step (IV) can be dissolved in methylene chloride at 0° C. A 100 ml quantity of boron tribromide (1M) in methylene chloride can be added slowly while keeping the temperature at 0° C. The mixture can be stirred at 0° C. for 24 hours. Then, the mixture can be washed with distilled water. The washed organic solution can be evaporated to obtain the crude product. The crude product can be purified by recrystallization from a mixture of heptane and methylene chloride at a volume ratio of 8:1, respectively.

Formation of the Polymer Charge Transport Material

In general, the reaction conditions can be selected to polymerize the monomer units when it is desired to form the polymer. For example, for embodiments in which the E group is an epoxy, the conditions can be made basic to catalyze the reaction. Other appropriate variations in the reaction conditions can be made for other functional groups. The degree of polymerization can be controlled by varying the reaction conditions, such as by the temperature, pH, solvent amount and/or the presence at a selected time and a selected concentration of a compound that terminated the polymerization reaction, such as a monofunctional alcohol for epoxy containing monomers.

The polymeric charge transport material can be combined with a polymeric binder and other desired compositions, as described above for the formation of the organophotoreceptor. In some embodiments, the charge transport material is crosslinked with the binder, which is selected to have crosslinkable functional groups, as described above. The polymerization reaction can be controlled to terminate with a selected portion of unreacted functional groups still present. These unreacted functional groups would then be available for reacting with the functional groups of the binder. In addition, the entire polymerization reaction can be carried out in the presence of the polymer binder. Performing the polymerization reaction in the presence of the polymer binder would tend to form an integrated crosslinked composition. The crosslinking/polymerization process can be controlled through adjusting of the concentration of the compositions within the solvent as well as the temperature and pH. The crosslinking/polymerization reaction can be performed to coincide with the coating process for embodiments in which the crosslinked composition becomes difficult to disperse or solubilize after the reaction is completed.

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:

(a) a charge transport material having the formula

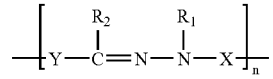

where X is a linking group having the formula —$(CH_2)_m$—, branched or linear, where m is an integer between 0 and 20, inclusive, and one or more of the methylene groups is optionally replaced by O, S, C=O, O=S=O, a heterocyclic group, an aromatic group, urethane, urea, an ester group, a $NR_3$ group, a $CHR_4$ group, or a $CR_5R_6$ group where $R_3$, $R_4$, $R_5$, and $R_6$ are, independently, H, hydroxyl group, thiol group, an alkyl group, an alkaryl group, a heterocyclic group, or an aryl group;

$R_1$ and $R_2$ are independently a hydrogen, a halogen, an alkyl group, an aryl group, an alkaryl group, an aromatic group or a heterocyclic group;

Y is a divalent aromatic linking group; and n is a distribution of integer values greater than 2; and (b) a charge generating compound.

2. An organophotoreceptor according to claim 1 wherein the photoconductive element further comprises an electron transport compound.

3. An organophotoreceptor according to claim 1 wherein Y comprises an N,N-disubstituted arylamine.

4. An organophotoreceptor according to claim 3 wherein the (N,N-disubstituted)arylamine group is a p-(N,N-disubstituted)arylamine group.

5. An organophotoreceptor according to claim 3 wherein the (N,N-disubstituted)arylamine group comprises a triphenyl amine group, a carbazole group or a julolidine group.

6. An organophotoreceptor according to claim 1 wherein the photoconductive element further comprises a polymer binder.

7. An organophotoreceptor according to claim 6 wherein the polymer binder is crosslinked with the charge transport material.

8. An organophotoreceptor according to claim 7 wherein the polymer binder and charge transport compound are crosslinked through a crosslinking agent.

9. An organophotoreceptor according to claim 1 wherein the charge transport material comprises an epoxy linkage.

10. An organophotoreceptor according to claim 9 wherein a crosslinking agent is bonded between the epoxy linkage and the polymer binder.

11. An organophotoreceptor according to claim 1 wherein the $R_1$ group is a phenyl group and $R_2$ is a hydrogen.

12. An electrophotographic imaging apparatus comprising:
(a) a light imaging component; and
(b) an organophotoreceptor oriented to receive light from the light imaging component, the organophotoreceptor comprising an electrically conductive substrate and a photoconductive element on the electrically conductive substrate, the photoconductive element comprising:
(i) a charge transport compound having the formula

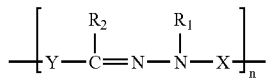

where X is a linking group having the formula $-(CH_2)_m-$, branched or linear, where m is an integer between 0 and 20, inclusive, and one or more of the methylene groups is optionally replaced by O, S, C=O, O=S=O, a heterocyclic group, an aromatic group, urethane, urea, an ester group, a $NR_3$ group, a $CHR_4$ group, or a $CR_5R_6$ group where $R_3$, $R_4$, $R_5$, and $R_6$ are, independently, H, hydroxyl group, thiol group, an alkyl group, an alkaryl group, a heterocyclic group, or an aryl group;

$R_1$ and $R_2$ are independently a hydrogen, a halogen, an alkyl group, an aryl group, an alkaryl group, an aromatic group or a heterocyclic group;

Y is a divalent aromatic linking group; and n is a distribution of integer values greater than 2; and
(ii) a charge generating compound.

13. An electrophotographic imaging apparatus according to claim 12 wherein Y comprises an N,N-disubstituted arylamine.

14. An electrophotographic imaging apparatus according to claim 13 wherein the (N,N-disubstituted)arylamine group comprises a triphenyl amine group, a carbazole group or a julolidine group.

15. An electrophotographic imaging apparatus according to claim 12 wherein the photoconductive element further comprises an electron transport compound.

16. An electrophotographic imaging apparatus according to claim 12 wherein the photoconductive element further comprises a binder.

17. An electrophotographic imaging apparatus according to claim 12 wherein the binder is crosslinked with the charge transport material.

18. An electrophotographic imaging apparatus according to claim 17 wherein a crosslinking agent forms chemical crosslinks between the charge transport material and the binder.

19. An electrophotographic imaging apparatus according to claim 12 further comprising a liquid toner dispenser.

* * * * *